(12) United States Patent
Wei et al.

(10) Patent No.: US 7,665,375 B2
(45) Date of Patent: Feb. 23, 2010

(54) FLOW SPLITTER FOR A SOLID PARTICLE COUNTING SYSTEM

(75) Inventors: Qiang Wei, Novi, MI (US); Scott T. Porter, Ann Arbor, MI (US); Ichiro Asano, Shiga (JP); Montajir M D. Rahman, Otsu (JP); Takeshi Kusaka, Otsu (JP)

(73) Assignee: Horiba, Ltd., Kyoto (JP)

( * ) Notice: Subject to any disclaimer, the term of this patent is extended or adjusted under 35 U.S.C. 154(b) by 504 days.

(21) Appl. No.: 11/614,450

(22) Filed: Dec. 21, 2006

(65) Prior Publication Data

US 2008/0148870 A1 Jun. 26, 2008

(51) Int. Cl.
*G01N 15/00* (2006.01)
(52) U.S. Cl. .................................... 73/865.5
(58) Field of Classification Search ................ 73/865.5, 73/118.2
See application file for complete search history.

(56) References Cited

U.S. PATENT DOCUMENTS

| | | | |
|---|---|---|---|
| 5,090,258 A | | 2/1992 | Yamasaki et al. |
| 5,188,510 A | * | 2/1993 | Norris et al. ............. 415/208.1 |
| 5,340,276 A | * | 8/1994 | Norris et al. ............. 415/208.1 |
| 5,603,604 A | * | 2/1997 | Norris et al. ............. 415/208.1 |
| 6,578,414 B2 | * | 6/2003 | Kohmura et al. .............. 73/202 |
| 6,647,776 B2 | * | 11/2003 | Kohmura et al. ......... 73/204.21 |
| 6,767,378 B2 | | 7/2004 | Nishiyama et al. |
| 6,857,327 B2 | | 2/2005 | Silvis et al. |
| 7,044,009 B2 | | 5/2006 | Graze, Jr. |
| 7,458,287 B2 | * | 12/2008 | Parfitt et al. ................ 73/865.5 |
| 2006/0179960 A1 | | 8/2006 | Wei |
| 2008/0148812 A1 | * | 6/2008 | Wei et al. ................... 73/23.31 |
| 2008/0148874 A1 | * | 6/2008 | Wei et al. ................... 73/865.5 |

OTHER PUBLICATIONS

"Real-time measuring system for engine exhaust solid particle number emission—Performance and Vehicle tests," SAE Technical Paper No. 2006-01-0865.
"Real-time measuring system for engine exhaust solid particle number emission—Design and Performance," SAE Technical Paper No. 2006-01-0864.

* cited by examiner

*Primary Examiner*—Hezron Williams
*Assistant Examiner*—Rodney T Frank
(74) *Attorney, Agent, or Firm*—Brooks Kushman P.C.

(57) ABSTRACT

A solid particle counting system for measuring solid particle number concentrations from engine or vehicle exhausts in real-time includes a flow splitter having an inlet, a sample outlet, and a by-pass outlet arranged such that a main flow enters the inlet and changes direction to exit the by-pass outlet. A sample flow from the main flow exits the sample outlet. The flow splitter further includes a guiding element arranged such that particles at a sampling location upstream of the main flow direction change are guided to the sample outlet.

14 Claims, 4 Drawing Sheets

FLOW SPLITTER FOR A SOLID PARTICLE COUNTING SYSTEM

BACKGROUND OF THE INVENTION

1. Field of the Invention

The invention relates to measuring solid particle number concentrations from engine or vehicle exhausts in real-time.

2. Background Art

Engine exhaust particles mainly consist of solid and volatile particles. Many studies show particles from diesel engine exhausts cause many health problems. To understand how particles impact human health, characteristics of particles from engines and vehicles should be investigated. Thus, the accurate measurement of particles emitted by modern diesel and gasoline vehicles is needed.

European PMP (Particle measurement programme) has recommended an approach to measure solid particle number emission from light-duty diesel vehicles. The system is shown in FIG. 1, and consists of a pre-classifier 10, a hot diluter (PND1) 12, an evaporation tube 14, a cold diluter (PND2) 16, and a condensation particle counter (CPC) 18. The pre-classifier 10 is used to keep the cutoff size of particles in 2.5 to 10 µm. By running the hot diluter 12 at a high dilution air temperature, and the evaporation tube 14 heating the sample in the range of 300 to 400° C., particles formed by volatile material and sulfate are vaporized to gas phase. By following with cold dilution with the cold diluter 16, all particles formed by volatile material and sulfate are removed. As a result, solid particles only move into the CPC 18 with the flow. The concentration of the solid particles is measured in the CPC 18.

Many factors, such as dilution ratios on the hot diluter (PND1) 12 and cold diluter (PND2) 16, solid particle penetration over the instrument, removal efficiency for volatile particles, etc., strongly influence the accuracy of the instrument. To have good accuracy on the measurement, accurate dilution ratios on the hot diluter (PND1) 12 and the cold diluter (PND2) 16, high penetration for solid particles, and high removal efficiency for volatile particles, should be achieved on the measuring system.

The condensation particle counter (CPC) has been widely used to measure particle number concentration. It has fast response time and is a real-time sensor. However, the experimental setup and operation procedure and calibration to use the CPC for measuring combustion engine or vehicle exhaust aerosols are pretty complicated. The accuracy of the measured results is strongly influenced by human factors, such as, the knowledge of the operator of combustion engines and aerosol science, etc. To make the CPC more reliable for engine or vehicle exhaust aerosol measurement, it is very important to simplify the experimental setup and operation procedure.

Background information may be found in U.S. Pub. No. 2006/0179960. This publication describes the concept of a wide range continuous diluter. Further background information may be found in "Real-time measuring system for engine exhaust solid particle number emission—Performance and Vehicle tests," SAE Technical Paper No. 2006-01-0865, and in "Real-time measuring system for engine exhaust solid particle number emission—Design and Performance," SAE Technical Paper No. 2006-01-0864.

SUMMARY OF THE INVENTION

It is an object of the invention to provide a reliable, repeatable, and easily operated instrument to measure solid particle emissions from engine or vehicle exhaust, and to use as an instrument for certification, and research and development.

The invention comprehends a solid particle counting system (SPCS) that in one embodiment comprises mass flow controllers, flow orifices, pressure sensors, thermocouples, ball valves, a cyclone, an evaporation tube, etc. The concept of a wide range continuous diluter is used on the hot diluter (PND1) and the cold diluter (PND2). These diluters give accurate and wide range dilution ratios while high solid particle penetrations are achieved. Due to real time dilution ratios available from the hot diluter (PND1) and the cold diluter (PND2), the instrument gives more accurate particle measurement in real time.

At the more detailed level, in the preferred embodiment, by turning on/off valves manually or automatically on the SPCS, the instrument can run in different modes, such as a sample mode, an idle mode, a daily calibration mode, zero and flow checks for the CPC, system zero check, and purge.

In accordance with one aspect of the invention, a solid particle counting system for measuring solid particle number concentrations from engine or vehicle exhausts in real-time includes a main flow and a sample flow from the main flow. The sample flow is directed to a particle counter. The system further comprises a flow splitter having an inlet, a sample outlet, and a by-pass outlet arranged such that the main flow enters the inlet and changes direction to exit the by-pass outlet. The sample flow from the main flow exits the sample outlet. The flow splitter further includes a guiding element arranged such that particles at a sampling location upstream of the main flow direction change are guided to the sample outlet.

It is appreciated that the guiding element may take a variety of forms. In one implementation, the guiding element further comprises a tube extending into the flow splitter from the sample outlet. The tube extends to a location upstream of the by-pass outlet. In another implementation, the guiding element further comprises a plate installed in the flow splitter at a location upstream of the by-pass outlet. The plate guides particles from the sampling location to the sample outlet.

DETAILED DESCRIPTION OF THE PREFERRED EMBODIMENTS

FIGS. 2-6 illustrate the preferred embodiment of a solid particle counting system (SPCS) made in accordance with the invention. It is to be appreciated that those skilled in the art may implement various aspects of the system in other ways and that the following description is intended to be exemplary and not intended to be limiting. Specifically, the following description relates to the preferred embodiment illustrated in FIGS. 2-6, and other embodiments of the invention may be implemented in other ways.

In the following description of the preferred embodiment, the work principle of the instrument is explained in three aspects, general description, detail components, and functions. To understand how the SPCS works, the three sections should be considered together.

General Description

Figure 2:
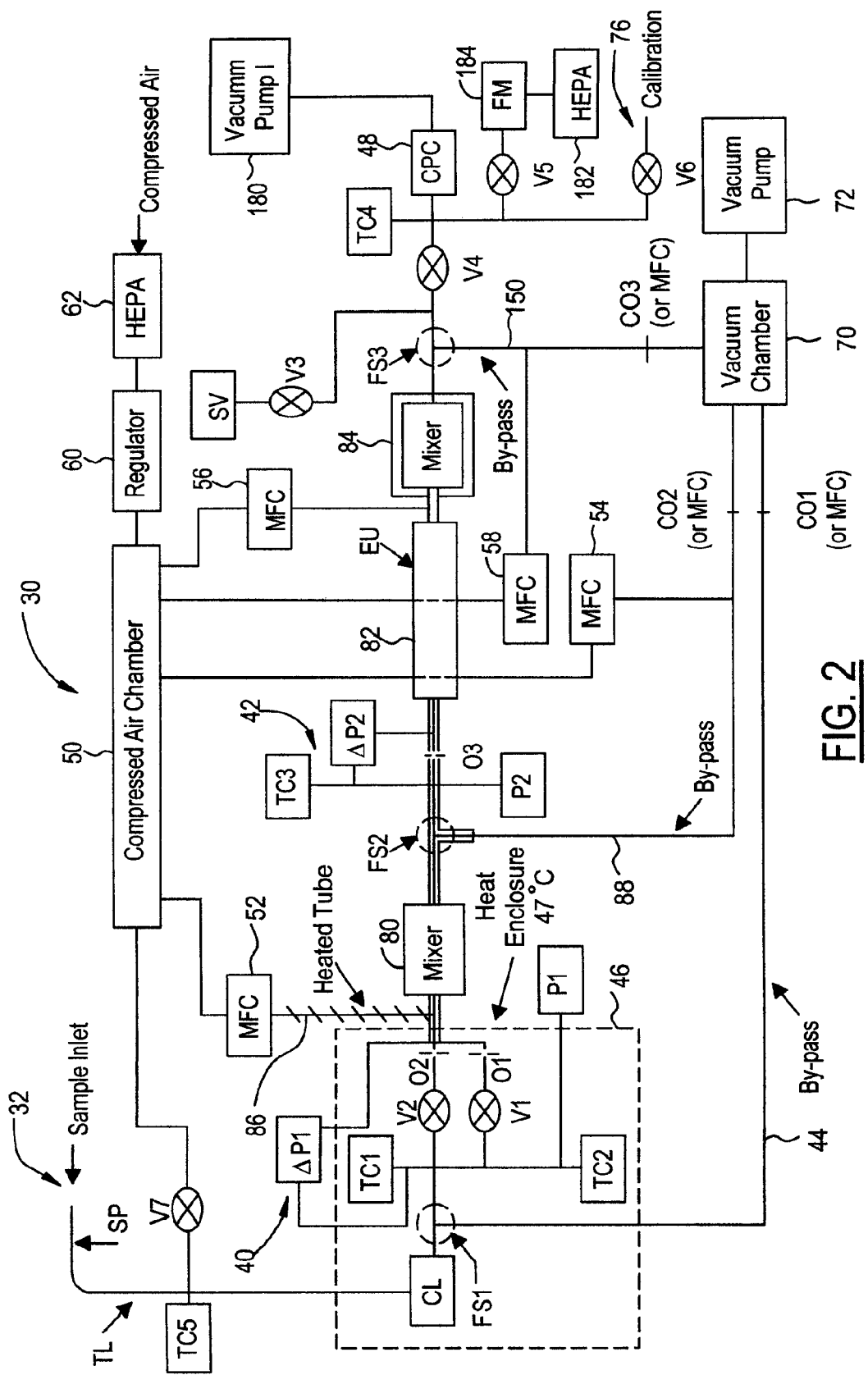
FIG. 2 is a flow schematic of a solid particle counting system (SPCS) according to a preferred embodiment of the invention.

With reference to FIG. 2, the solid particle counting system (SPCS) in the preferred embodiment is generally indicated at 30. The SPCS sample inlet is indicated at 32. SPCS 30 includes various components, generally described below.

Ball valves, V1, V2, V4, V6, and V7, are normally-closed valves. These valves can be operated manually or automatically, for example, air or electrically actuated. Ball valves V3 and V5 are normally-open valves. In the same way as the other ball valves, these valves can be operated manually or automatically. There are no flow restrictions while ball valves are opened. Thus, the ball valves do not result in particle losses while particles move through them. A solenoid valve SV is a normally-open valve. The solenoid valve SV is closed when the solenoid is energized. By opening or closing valves, the SPCS 30 can be operated for different functions.

A first orifice flow meter 40 is composed of thermocouples TC1 and TC2, ball valves V1 and V2, orifices O1 and O2, absolute pressure transducer P1, and differential pressure transducer ΔP1. Thermocouples TC1 and TC2 measure flow temperatures upstream of ball valves V1 and V2, respectively. The absolute pressure transducer, P1, measures the absolute pressure in the flow. The differential pressure transducer, ΔP1, measures the pressure difference over orifice O1 or O2. For example, ΔP1 measures pressure difference over orifice O1 when ball valve V1 is open and ball valve V2 is closed; ΔP1 measures pressure difference over orifice O2 when ball valve V2 is open and ball valve V1 is closed. The status of V1 and V2 is determined by the status of the instrument. Orifice flow meter 40 is calibrated by a precise flow meter. The volume flow through O1 or O2 is a function of the pressure difference over O1 and O2. The mass flow rate can be calculated from the flow temperature and absolute pressure. Two calibration curves which are in polynomial equations are established for O1 and O2, respectively. When O1 is picked up, the calibration curve for O1 is used to calculate the flow. In opposite, the calibration curve for O2 is used to calculate the flow when O2 is picked up.

A second orifice flow meter 42 is composed of a thermocouple TC3, an absolute pressure transducer P2, a differential pressure transducer ΔP2, and an orifice O3. The calibration procedure of orifice flow meter 42 is as same as above. To minimize the heat transfer between the flow meter 42 and ambient, it is insulated. As a result, particle losses due to thermophoresis are minimized.

A cyclone (CL), ball valves V1 and V2, orifices O1 and O2, thermocouples TC1 and TC2, and a part of by-pass 44 are installed in a heat enclosure 46. The heat enclosure 46 is heated by a heater and the temperature is controlled at constant temperature, 47° C., by a temperature controller. The status of V1 and V2 (open or closed) is determined by the status of the instrument. Since the heat enclosure 46 is controlled at a constant temperature, the flow through orifice O1 or orifice O2 is maintained at the constant temperature as well. As a result, the fluctuation of the flow through orifice flow meter 40 due to temperature variations is minimized.

Thermocouple TC5 measures the sample temperature (near sample inlet 32), and thermocouple TC4 measures the temperature of the flow which moves into the CPC 48. Both temperatures are monitored carefully during the test.

The compressed air chamber 50 is the source of the compressed air supply for the instrument. Compressed air chamber 50 supplies particle free compressed air for mass flow controllers 52, 54, 56, 58 and ball valve V7. A regulator 60 is installed upstream of the chamber 50, and controls compressed air pressure at a desired value. A high efficiency particle air filter (HEPA) 62 removes particles from the compressed air. As a result, the compressed air in the chamber 50 is particle free.

Vacuum chamber 70 is the source of vacuum, and is connected to a vacuum pump 72. Chamber 70 draws flow from critical orifices C01, CO2, and CO3. Those critical orifices control flow through each flow route as constant. Alternatively, the critical orifices can be replaced by mass flow controllers. The advantage of the critical orifice for the flow control is that the cost of the critical orifice is much less than that of the mass flow controller. However, the critical orifice requires much stronger vacuum pump and the volume flow is fixed as well. For the mass flow controller, it provides a wide flow range, and a much smaller vacuum pump can be used with it to maintain the same level of flow as a critical orifice.

All tubings and fittings which contact to aerosol flow are made by stainless-steel. The stainless-steel material has good electrical conductivity and chemical resistance, and can minimize particle losses by electrostatic. In FIG. 2, tubings and fittings for flow routes, sample inlet 32→sample probe SP→transfer line TL→cyclone CL→ball valve V2 (V1)→orifice O2 (O1)→Mixer 80→orifice O3→evaporation unit 82→Mixer 84→ball valve V4→CPC 48, and Calibration port 76→ball valve V6→CPC 48, are stainless-steel.

Since a high temperature aerosol moves into orifice O2 (O1)→Mixer 80→orifice O3→evaporation unit 82→Mixer 84, tubings and fittings are well insulated to minimize heat transfer. As a result, particle losses are minimized as well.

Figure 3:
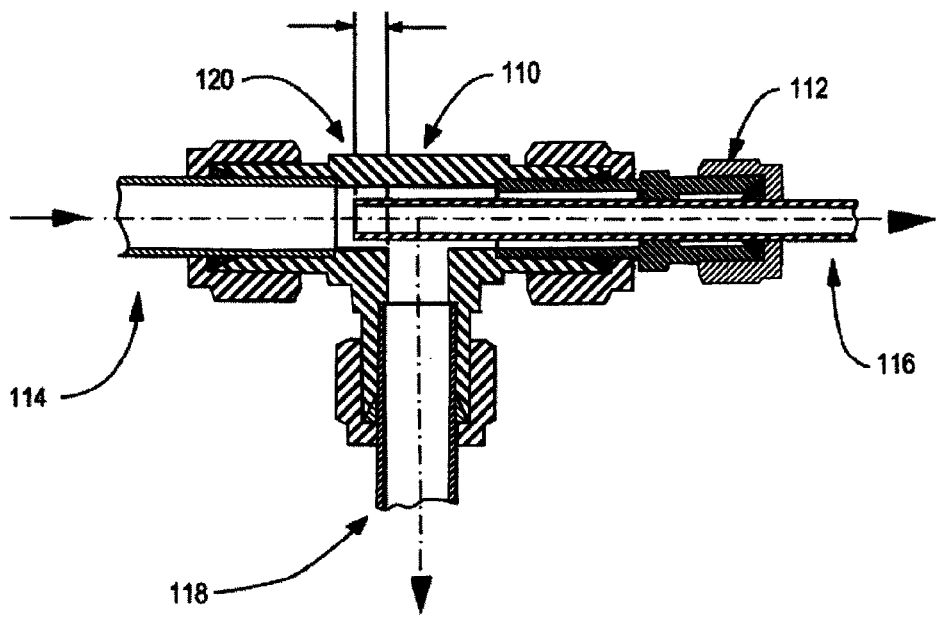
FIG. 3 is a cross-sectional view of a flow splitter in the solid particle counting system (SPCS)

Flow splitters, FS1, FS2, and FS3, are designed to minimize large size particle over sampled due to main flow direction change. FIG. 3 shows the schematic for this design in the preferred embodiment. The flow splitter consists of a ½" stainless-steel union Tee 110, a ½" to ¼" bore through reducer 112, a flow inlet 114, a flow outlet 116, and a by-pass 118. For the flow inlet 114 and by-pass 118, they are ½" stainless-steel tubings. For the flow outlet 116, it is a ¼" stainless-steel tubing. The ¼" stainless-steel tubing extends into the union Tee 110 through the bore through reducer 112. The length of the ¼" stainless-steel tubing exceeding (120) the left-side wall of the union Tee 110 is 0.1969" or 5 mm. The aerosol flow moves into the splitter from the flow inlet 114. A large fraction of flow leaves the splitter from the by-pass 118. A small fraction of flow moves into other devices through the flow outlet 116. Since the flow outlet 116 takes sample from the location up-stream of the by-pass 118, it avoids over sampling large size particles due to the main stream direction changed at the by-pass 118.

Figure 7:
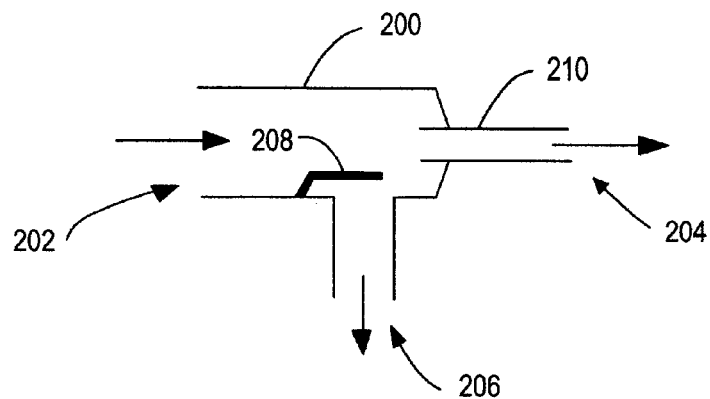
FIG. 7 is a schematic for an alternative embodiment of a flow splitter in the solid particle counting system (SPCS).

FIG. 7 shows the schematic for the flow splitters, FS1, FS2, and FS3, in an alternative embodiment. Flow splitter 200 includes a flow inlet 202, a flow outlet 204, and a by-pass 206. A plate 208 is installed in flow splitter 200 at a location upstream of by-pass 206. The plate 208 composes a guiding element that guides particles from the sampling location to the sample outlet 204. Tube 210 extends into the flow splitter 200 toward plate 208.

In more detail, flow splitters FS1, FS2, and FS3 include a guiding element that guides particles from the sampling location to the sample outlet. The sampling location is located upstream of the by-pass. By sampling upstream of the by-pass, an accurate, representative sample is taken, and over-sampling large size particles is avoided. That is, the main stream direction change at the by-pass, if the guiding element were omitted, could result in large size particles being over-represented in the sample flow because such particles with larger inertial force would not be as responsive to the main flow direction change as smaller particles.

In the FIG. 3 embodiment, the guiding element is achieved by the extension of flow outlet tubing 116 to the sampling location upstream of by-pass 118, thereby sampling the flow prior to the main stream direction change. In the FIG. 7 embodiment, plate 208 is installed upstream of by-pass outlet 206 to guide particles from the sampling location to sample outlet 204. That is, plate 208 assures that large particles are not over-sampled.

Detail Components

Figure 1:
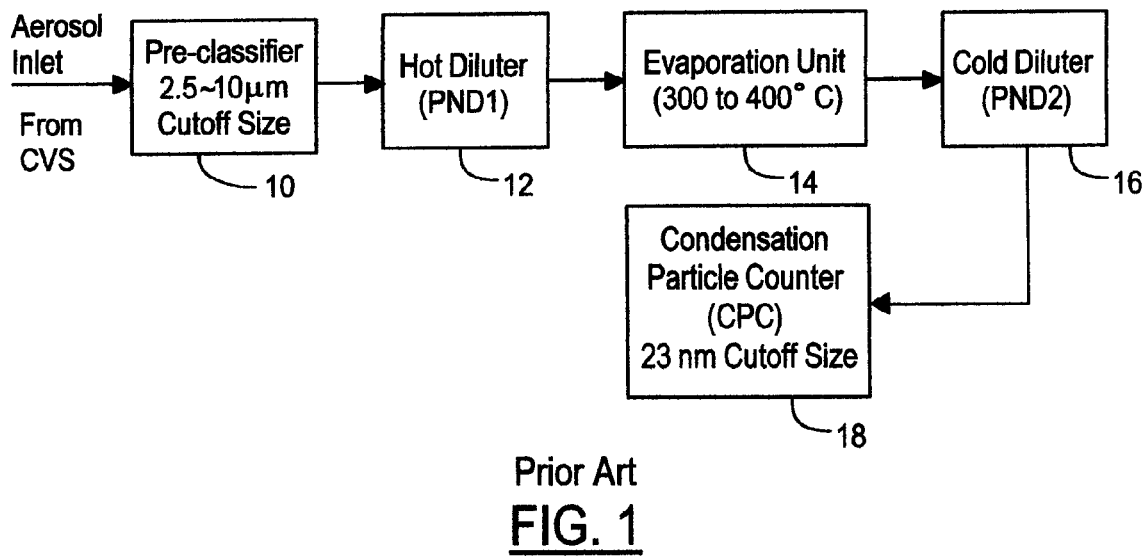
FIG. 1 is a block diagram of a solid particle counting system (SPCS) according to the European PMP recommended approach.

FIG. 1 illustrates the SPCS, according to the European PMP recommended approach, in block diagram form composed of the sample inlet, pre-classifier 10, hot diluter (PND1) 12, evaporation unit (EU) 14, cold diluter (PND2) 16, and CPC 18. These components are implemented in the SPCS 30 of FIG. 2, according to the preferred embodiment of the invention, as described in detail below.

a. Sample Inlet

The sample inlet consists of sample probe SP, transfer line TL, and thermocouple TC5. The sample probe receives a diluted diesel aerosol from a constant volume sampler (CVS) or a partial flow diluter. The aerosol moves in the transfer line to a pre-classifier. TC5 measures the temperature of the aerosol.

b. Pre-Classifier

The pre-classifier consists of stainless-steel cyclone CL, flow splitter FS1, by-pass 44, and critical orifice CO1 (or a mass flow controller). The cyclone gives a particle cutoff size between 2.5 and 10 μm which depends on the flow rate of by-pass 44. By using a different size critical orifice CO1 or setting different flow on the mass flow controller, different cutoff size on particles can be obtained.

The flow splitter, FS1, which is described above, is connected to the cyclone CL. There are two outlets on the flow splitter. One is connected to by-pass 44, and the other is connected to the inlet of orifice flow meter 40. A big fraction of the flow moves out through by-pass 44 while a small fraction of the aerosol flows into orifice flow meter 40. The residence time of aerosol in the transfer line TL and sample probe SP is minimized due to the large by-pass flow (by-pass flow 44). As a result, particle losses by diffusion are minimized in the transfer line TL and the sample probe SP. Since the aerosol into orifice flow meter 40 is taken upstream of the by-pass 44, this minimizes the probability of large size particles being over sampled, due to 90 degree turning of the flow direction.

The pre-classifier except CO1 (or mass flow controller (MFC)) is installed in the heat enclosure 46. The temperature of the heat enclosure 46 is maintained at a constant, such as, 47° C. The flow in the pre-classifier maintains at a constant temperature. As a result, the aerosol with a constant temperature is supplied to orifice flow meter 40. This design avoids the fluctuation of test results due to temperature variations from test to test.

c. Hot Diluter (PND1)

Figure 4:
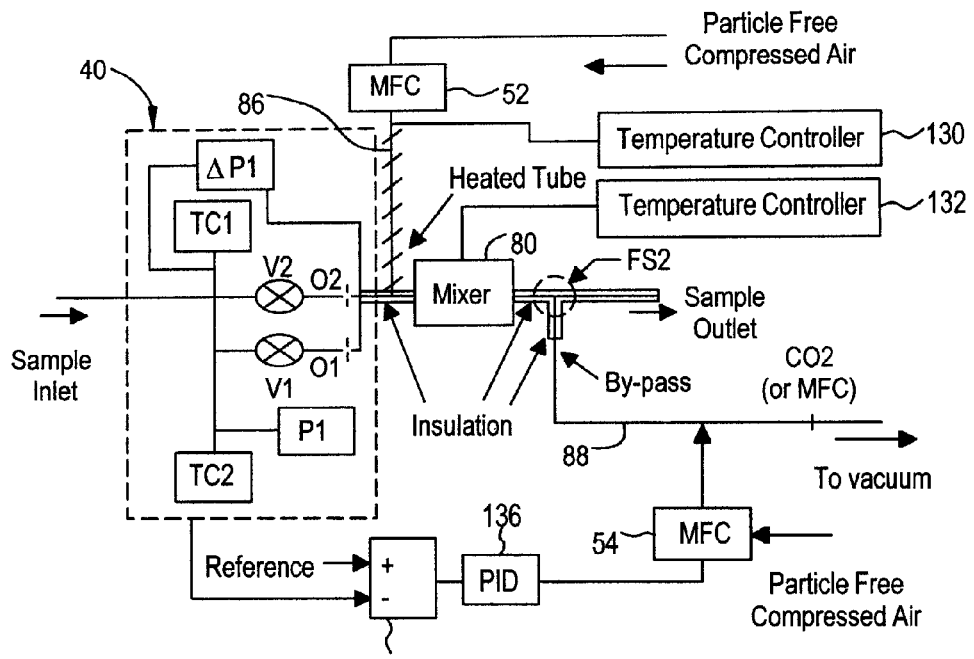
FIG. 4 is a schematic for the hot diluter (PND1) in the solid particle counting system (SPCS)

With reference to FIGS. 2 and 4, the hot diluter (PND1) consists of orifice flow meter 40, mass flow controllers MFC 52 and MFC 54, heated tube 86, Mixer 80, by-pass 88, critical orifice CO2 (or mass flow controller), flow splitter FS2, temperature controllers 130 and 132, and a PID loop (summer 134, PID 136).

Orifice flow meter 40 measures an aerosol mass flow rate in real-time. The mass flow controller (MFC) 52 controls the dilution air flow. MFC 52 receives the particle free dilution air from the compressed air chamber 50. The heated tube 86 heats the dilution air temperature in the range of 150 to 190° C. The temperature of the dilution air is controlled by temperature controller 130. Mixer 80 is wrapped with a heating tape, and the temperature is controlled by temperature controller 132. The aerosol temperature in the mixer is controlled as same as that of the dilution air. The aerosol flow and the dilution air flow are mixed in the mixer 80 uniformly. Equation 1 shows the calculation of the dilution ratio on the PND1. Based on equation 1, the dilution ratio on the PND1 can be adjusted by either adjusting dilution air flow or sample flow or both. By adjusting flow setting manually or automatically on MFC 52, the dilution air flow can be changed. The sample flow can be adjusted by changing the flow rate (make up air) on MFC 54. For example, by increasing the flow rate on MFC 54, the flow rate of the sample flow can be decreased. By decreasing the flow rate on MFC 54, the flow rate of the sample flow can be increased. The air flow on MFC 54 is supplied by the compressed air chamber. According to equation 1, $$DR_{PND1} = \frac{Q_{air1}}{Q_{s1}} + 1 \tag{1}$$

where $DR_{PND1}$ is the dilution ratio on the PND1, $Q_{air1}$ is the flow rate of the dilution air at the standard or a reference condition, $Q_{s1}$ is the aerosol flow rate at the standard or a reference condition, $Q_{s1}$ is measured by orifice flow meter 40.

The inlet of the flow splitter FS2 is connected to the outlet of the mixer 80. The mixture of the dilution air and the aerosol flow moves through the splitter FS2. A big fraction of the mixture moves into the vacuum chamber through by-pass 88 and critical orifice CO2 or mass flow controller. A small fraction of flow moves into orifice flow meter 42 through the other outlet of the flow splitter. The unique design of the flow splitter minimizes the probability of the large size particles being over sampled due to flow direction change at the inlet of by-pass 88.

Two flow orifices, O1 and O2, are enclosed in orifice flow meter 40. To minimize particle losses caused by particle diffusion, the residence time of aerosol in the flow meter is reduced by shorting the tubing length and using right inside diameter stainless-steel tubing. Each orifice covers a range of aerosol sample flow. For example, based on the desired dilution ratio, the sample flow can be calculated from equation 1 while the dilution air flow is set at the desired value. If the sample flow rate is falling into the flow range covered by O1, the calibration curve for O1 is used. Thus, ball valve V1 is open and ball valve V2 is closed manually or automatically. In other cases, O2 is picked up, and ball valve V2 is open and ball valve V1 is closed manually or automatically. Since multiple orifices (could be over two orifices) are enclosed in orifice flow meter 40, PND1 provides a wide dilution ratio range.

Orifice flow meter 40 is installed in the heat enclosure 46. As mentioned above, the heat enclosure 46 is controlled at a constant temperature. Thus, the aerosol temperature in the orifice flow meter is constant as well. As a result, it minimizes the flow variation caused by temperature and gets rid of particle concentration variation by temperature as well. This design gives an advantage on the repeatability of the instrument.

To ensure accurate dilution ratios are obtained during engine or vehicle tests from PND1, a PID loop (summer 134, PID 136) is integrated in the system to keep the aerosol flow at constant by adjusting the flow on MFC 54. For example, when the sample flow is higher than a set point, the PID loop drives MFC 54 to increase the flow. When the sample flow is lower than a set point, the PID loop drives MFC 54 to decrease the flow. As a result, the dilution ratio on the PND1 is kept at constant. Thus, the accurate result can be obtained from the instrument while the flow conditions such as temperature and pressure are fluctuated in the sample inlet. FIG. 4 shows the schematic for this control.

The orifice flow meter 40 measures the aerosol flow accurately and does not result in particle losses. Therefore, PND1 provides real-time accurate dilution ratio and gives high penetration to particles.

d. Evaporation Unit (EU)

Figure 5:
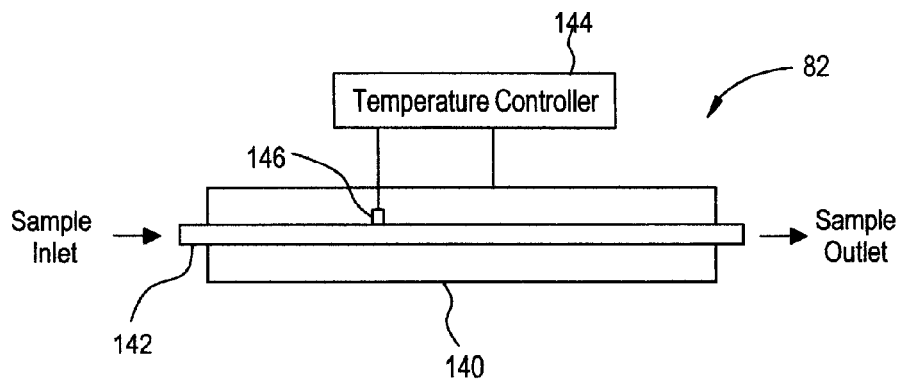
FIG. 5 is a schematic for the evaporation unit in the solid particle counting system (SPCS)

FIG. 5 shows the schematic of the evaporation unit 82. The evaporation unit 82 includes insulation and heating tape 140, stainless-steel tubing 142, and temperature controller 144.

A heating tape is wrapped on the stainless-steel tubing 142 to ensure uniform wall temperature over the length. Temperature controller 144 controls the wall temperature in the range of 300 to 400° C. A thermocouple 146 measures wall temperature, and sends a signal to the temperature controller 144. To minimize the heat transfer between the EU 82 and the ambient air, the EU 82 is insulated well.

While aerosol moves through the EU 82, volatile particles are vaporized to gas phase. Solid particles in the aerosol flow through the EU 82 without particle losses. Then, following a cold dilution from the cold diluter (PND2), the aerosol temperature is decreased below 35° C., and volatile particles are removed from the aerosol.

f. Cold Diluter (PND2)

The cold diluter consists of orifice flow meter 42, mass flow controllers MFC 56 and MFC 58, mixer 84, flow splitter FS3, by-pass 150, and critical orifice CO3 (or a mass flow controller).

Orifice flow meter 42 is insulated and installed upstream of the evaporation unit 82. Orifice flow meter 42 measures aerosol flow into the PND2 and the evaporation unit 82. By installing orifice flow meter 42 upstream of the evaporation unit 82, it minimizes the flow measurement errors caused by high temperature aerosol since the temperature upstream of the EU 82 is much lower than that of the downstream of the EU 82. The flow measurement errors caused by the high temperature may include the flow variation due to the shape and the size of the stainless-steel orifice changed under high temperatures. Thus, by installing orifice flow meter 42 upstream of the EU 82, more accurate and consistent flow measurement is obtained.

The dilution air temperature on the cold diluter is the same as that in the ambient air. The flow rate of the dilution air is controlled by a mass flow controller, MFC 56. As same as PND1, the dilution ratio on the PND2 is controlled by adjusting either dilution air flow from MFC 56 or make up air flow from MFC 58. For example, at a constant dilution air flow, the aerosol flow through orifice flow meter 42 is increased while the make up air flow from MFC 58 is decreased. In other words, the aerosol flow through orifice flow meter 42 is decreased while the make up air flow from MFC 58 is increased. As a result, dilution ratios on the PND2 are adjusted. Equation 2 shows the dilution ratio from the PND2, and equation 3 presents total dilution ratio calculation for the instrument.

$$DR_{PND2} = \frac{Q_{air2}}{Q_{s2}} + 1 \quad (2)$$

$$DR = DR_{PND1} \times DR_{PND2} \quad (3)$$

where $DR_{PND2}$ is the dilution ratio on the cold diluter (PND2), $Q_{air2}$ is the dilution air flow rate on the PND2 at the standard or reference conditions, $Q_{s2}$ is the aerosol flow moving through orifice flow meter 42, DR is the total dilution ratio on the SPCS.

The flow splitter, FS3, is connected to Mixer 84 at one side. Mixer 84 is well insulated to minimize the heat transfer between the mixer and ambient air. Dilution air controlled by MFC 56 and aerosol flow measured by orifice flow meter 42 are mixed uniformly in Mixer 84. One outlet of the flow splitter FS3 is connected to by-pass 150. A big fraction of the mixture moves through it. The flow through by-pass 150 is controlled by critical orifice C03. C03 could be replaced by a mass flow controller. The other outlet of the flow splitter FS3 is connected to the inlet of the CPC 48 through a ball valve, V4. A small fraction of the aerosol flows through it. Since it takes sample upstream of by-pass 150, it avoids large size particles being over sampled due to the direction change of the main stream of the aerosol flow.

Figure 6:
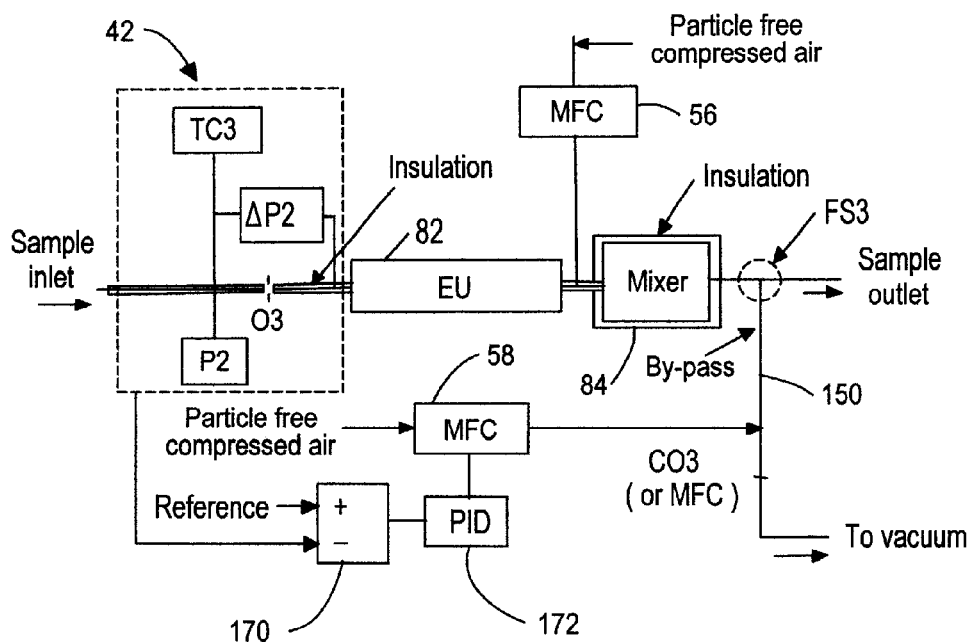
FIG. 6 is a schematic for the cold diluter (PND2) in the solid particle counting system (SPCS)

To have a constant dilution ratio from PND2, a PID loop (summer 170, PID 172) is integrated in the PND2 to ensure the dilution ratio running at the desired set point, as illustrated in FIG. 6.

g. Condensation Particle Counter (CPC)

The condensation particle counter (CPC) 48 is a particle sensor to measure particle number concentrations. CPC 48 is a real-time instrument. Many companies manufacture a suitable CPC.

For some CPC, there is no internal vacuum pump. To draw a sample into the instrument, an external pump is required. Vacuum pump 180 (Vacuum pump I) in FIG. 2 is prepared for a CPC without an internal pump. For a CPC with an internal pump, vacuum pump 180 can be removed.

A thermocouple, TC4, measures the aerosol temperature into the CPC 48. This temperature is monitored during the test. CPC 48 provides a well-defined (for example, constant) instrument flow.

Functions

When the SPCS 30 main power is turned on, SPCS 30 needs to be warmed up for about 15 minutes. During the warm-up, the CPC 48 is warmed up and all heated parts are controlled to set points. If the CPC 48 has an internal vacuum pump, vacuum pump 180 can be removed from the system. If CPC 48 does not have an internal vacuum pump, vacuum pump 180 is used to draw the aerosol through the CPC 48. At this circumstance, vacuum pump 180 is on as well for the warm-up.

a. Idle Mode

After the main power on the CPC 48 is on and warmed for about 15 minutes, the SPCS 30 enters the idle mode.

At the idle mode, no ball valves are energized or manually turned on/off. They stay at their original statuses. A flow moves from: HEPA 182→flow meter (FM) 184→ball valve V5→CPC 48.

HEPA 182 is a high efficiency particle filter. HEPA 182 provides a flow inlet, and removes particles from the inlet flow. Then the particle free flow moves into flow meter (FM) 184. After that, the flow moves through ball valve V5. V5 is a normally-open ball valve. Finally, the flow moves into the CPC 48. HEPA 182 protects the CPC 48 from contamination in the idle mode. Table 1 shows the status of valves and vacuum pumps for the idle mode.

TABLE 1

Status of valves and vacuum pump for the idle mode

| | V1 | V2 | V3 | V4 | V5 | V6 | V7 | SV | Vacuum pump I | Vacuum pump |
|---|---|---|---|---|---|---|---|---|---|---|
| Idle mode | | | | | | | | | X | |

X - For valves, it means the valve is energized or off the original status. For pumps, it means the pump is on.

b. CPC Zero and Flow Check

The CPC zero is defined as the verification of the measured particle concentration by the CPC 48 while particle free gas is sent into the CPC 48. The reading should be zero if there is no leak on the CPC 48. The flow check is defined as the verification of the aerosol flow of the CPC 48.

European PMP recommends that the CPC 48 should have a zero check prior to each day test. The aerosol flow into the CPC 48 (CPC flow check) should be verified as well. The flow rate can be off a few percents from the manufacturer's flow specification.

Those two functions have been combined as one function on the SPCS 30. The flow route is the same as that of the idle mode. Thus, the flow direction is: HEPA 182→FM 184→ball valve V5→CPC 48. No ball valves are energized or turned on/off manually. This function, which combines the CPC zero and the CPC flow check, makes CPC zero and flow check more efficient.

There is no difference for the flow route between the idle mode and CPC zero and flow check. The main difference between the two modes is the data acquisition if the SPCS 30 has a data acquisition system. When the SPCS 30 runs at CPC zero and flow check, the concentrations measured by the CPC 48 and the CPC inlet flow measured by the flow meter (FM) 184 are recorded by the data acquisition system. If there is not a data acquisition system on the SPCS 30, the concentrations and flows may be recorded manually. At the idle mode, the above actions are not necessary. Table 2 shows the status of valves and vacuum pumps at this mode.

TABLE 2

Status of valves and vacuum pumps for the CPC zero and flow check

| | V1 | V2 | V3 | V4 | V5 | V6 | V7 | SV | Vacuum pump I | Vacuum pump |
|---|---|---|---|---|---|---|---|---|---|---|
| Idle mode | | | | | | | | | X | |

X - For valves, it means the valve is energized or off the original status. For pumps, it means the pump is on.

c. System Zero Check

The system zero check is defined as the verification of the measured particle concentration while the particle free gas enters from the inlet of the SPCS 30. If there is no leakage in the SPCS 30, the reading of the CPC 48 should be zero. If the reading of the CPC 48 is not zero and larger than a critical value, serous leaks may be in the system. Thus, the instrument should be served to remove leaks. Based on the PMP recommendation, this critical value is 10 particles/cc.

When this mode is running, the vacuum pump 72 which is connected to the vacuum chamber 70 is turned on. When the vacuum pump 72 is turned on, a big pressure pulse is generated. As a result, the pressure at the inlet of the CPC 48 may be lower than that specified by the CPC manufacturer. If this happens, the work fluid in the CPC 48 may be sucked out from the CPC inlet, and enter some components in the SPCS 30, such as ball valve V4, flow splitter FS3, Mixer 84, etc. To avoid this issue, a solenoid valve (SV) and a ball valve V3 are installed.

Before the start of this mode, dilution air flows and dilution ratios on the hot diluter (PND1) and the cold diluter (PND2) should be set at some values. Once this mode is run, the two PID loops, one for PND1, and the other for PND2, drive MFC 54 and MFC 56 to run dilution ratios on PND1 and PND2 to desired values, respectively.

At the start of this mode, the vacuum pump 72 is turned on. There are two major flow routes ending at the CPC 48. One is solenoid valve SV→ball valve V3→ball valve V4→CPC 48, and the other one is compressed air chamber 50→ball valve V7→cyclone CL→ball valve V2 (V1) →orifice O2 (O1) → Mixer 80→orifice O3→evaporation unit (EU) 82→Mixer 84→ball valve V4→CPC 48.

The solenoid valve SV and ball valve V3 are normally open valves. Due to this flow route, it minimizes the pressure pulse caused by the starting of the vacuum pump 72 to the CPC 48. The SV keeps open for 5 to 30 seconds, and the open time can be decided by the operator or integrated in the control software. After the vacuum pump 72 is stabilized, the SV is energized and is closed. Thus, the flow route, solenoid valve SV→ball valve V3→ball valve V4→CPC 48, is turned off. Ball valve V3 can be turned off or kept on. The purpose to install ball valve V3 upstream of the solenoid valve SV is to shut off this flow route once the solenoid valve SV is failed or a leakage is detected on the solenoid valve SV. With this design (flow route SV→V3→V4→CPC), the issue of the CPC work fluid moving out from the inlet of the CPC 48 is solved.

After the flow route SV→V3→V4→CPC is turned off, there is only one flow route to the CPC 48. It is: compressed air chamber 50→ball valve V7→cyclone CL→ball valve V2 (V1)→orifice O2 (O1) →Mixer 80→orifice O3 evaporation unit (EU) 82→Mixer 84→ball valve V4→CPC 48. As mentioned above, the compressed air in the compressed air chamber 50 is particle free. When this mode is running, the particle free compressed air moves through ball valve V7 into the cyclone (CL). To ensure only particle free compressed air into orifice flow meter 40, equation 4 should be satisfied; otherwise, aerosol with particles may move into the system from the sample probe (SP). By adjusting the compressed air pressure from the regulator 60, equation 4 can be satisfied easily.

$$Q_{V7} \geq Q_{bypassI} + Q_{s1} \tag{4}$$

where $Q_{V7}$ is the flow rate of the particle free compressed air through V7, $Q_{bypassI}$ is the flow through critical orifice CO1 (or mass flow controller), $Q_{s1}$ is the sample flow into orifice flow meter 40.

If there are no particles detected by the CPC 48, it means there is no leak in the system. If the number concentration on the CPC 48 is higher than the CPC noise level, some leaks are in the system. They should be removed before vehicle or engine tests are run.

In summary, table 3 presents the status of ball valves and vacuum pumps. If the column is empty, valves stay at the original status.

TABLE 3

Status of valves and vacuum pump

| | V1 | V2 | V3 | V4 | V5 | V6 | V7 | SV | Vacuum pump I | Vacuum pump |
|---|---|---|---|---|---|---|---|---|---|---|
| Start of the mode | X | | | X | X | | X | | X | X |
| After 5 to 30 seconds (Option I) | X | | | X | X | | X | X | X | X |
| After 5 to 30 seconds (Option II) | X | | X | X | X | | X | X | X | X |

X - For valves, it means the valve is energized or off the original status. For pumps, it means the pump is on.

d. Daily Calibration for the CPC

The daily calibration for the CPC 48 is defined as the verification of the CPC linearity. European PMP recommends it should be done prior to the daily test.

Before this mode is run, an external unit which is able to provide constant particle concentrations from 0 to 100% of the maximum concentration is connected to the calibration port 76.

When this mode is run, the flow route is: Calibration port 76→ball valve V6→CPC 48. Table 4 shows the summary for valve status.

TABLE 4

Status of valves and vacuum pump for the daily calibration for the CPC

| | V1 | V2 | V3 | V4 | V5 | V6 | V7 | SV | Vacuum pump I | Vacuum pump |
|---|---|---|---|---|---|---|---|---|---|---|
| Daily calibration for the CPC | | | | | X | X | | | X | |

X - For valves, it means the valve is energized or off the original status. For pumps, it means the pump is on.

e. Sample Mode

The sample mode is defined as the SPCS 30 is taking sample from sample inlet 32. Aerosol moves into the system from the sample probe SP. All temperatures, number concentrations, flows etc. are recorded manually or by a data acquisition system.

As same as the mode called "system zero check", when this mode is running, the vacuum pump 72 which is connected to the vacuum chamber 70 is turned on. When the vacuum pump 72 is turned on, the big pressure pulse is generated. As a result, the pressure at the inlet of the CPC 48 may be lower than that specified by the CPC manufacturer. If it happens, the work fluid in the CPC 48 may be sucked out from the CPC inlet, and enters some components in the SPCS 30, such as ball valve V4, flow splitter FS3, Mixer 84, etc. To resolve this issue, the solenoid valve SV and ball valve V3 are utilized.

Before the start of this mode, the system should be warmed up. Temperatures on evaporation unit 82, mixer 80, PND1 dilution air and heat enclosure 46 should achieve set points. Dilution air flows and dilution ratios on the hot diluter (PND1) and the cold diluter (PND2) should be set at some values. When this mode is run, the two PID loops, one for PND1, and the other for PND2, drive MFC 54 and MFC 56 to run dilution ratios on PND1 and PND2 to desired values, respectively.

At the start of this mode, the vacuum pump 72 is turned on. There are two flow routes in the SPCS 30 to the CPC 48. One is solenoid valve SV→ball valve V3→ball valve V4→CPC 48, and the other is Sample inlet 32→sample probe SP→transfer line TL→cyclone CL→ball valve V2 (V1)→orifice O2 (O1)→Mixer 80→orifice O3→evaporation unit 82→Mixer 84→ball valve V4→CPC 48. Based on the desired dilution ratio, orifice O1 or O2 is determined. If the orifice O1 is picked up, ball valve V1 is open and ball valve V2 is closed. In opposite, if the orifice O2 is picked up, ball valve V2 is open and ball valve V1 is closed.

The solenoid valve SV and ball valve V3 are normal open valves. Due to this flow route, it minimizes the pressure pulse caused by the starting of the vacuum pump 72 to the CPC 48. The solenoid valve SV keeps open for 5 to 30 seconds, and the open time can be decided by the operator or integrated in the control software. After the vacuum pump 72 is stabilized, the solenoid valve SV is energized and is closed. Thus, the flow route, solenoid valve SV→ball valve V3→ball valve V4→CPC 48, is turned off. Ball valve V3 can be turned off or kept on. The purpose to install ball valve V3 upstream of the solenoid valve SV is to shut off this flow route while the solenoid valve SV is failed or leakage is detected on the solenoid valve SV. With this design (flow route SV→V3→V4→CPC), the issue of the CPC work fluid moving out from the inlet of the CPC is solved.

After the flow route SV→V3→V4→CPC 48 is turned off, there is only one flow route to the CPC 48. It is: Sample inlet 32→sample probe SP→transfer line TL→cyclone CL→ball valve V2 (V1) →orifice O2 (O1)→Mixer 80→orifice O3→evaporation unit 82→Mixer 84→ball valve V4→CPC 48. During the sample mode, the dilution ratio on the system can be adjusted by changing dilution air flows on PND1 and PND2 and changing make up air flows on MFC 54 and MFC 58. Table 5 shows the summary of the status of valves and pumps.

TABLE 5

Status of valves and vacuum pumps for the sample mode

| | V1 | V2 | V3 | V4 | V5 | V6 | V7 | SV | Vacuum pump I | Vacuum pump |
|---|---|---|---|---|---|---|---|---|---|---|
| Start of the mode (Option I) | X | | | X | X | | | | X | X |
| Start of the mode (Option II) | | X | | X | X | | | | X | X |
| After 5 to 30 seconds (Option I) | X | | | X | X | | X | X | X | X |
| After 5 to 30 seconds (Option II) | | X | | X | X | | X | X | X | X |

X - For valves, it means the valve is energized or off the original status. For pumps, it means the pump is on.
Option I - Based on the dilution ratio, orifice O1 is chosen.
Option II - Based on the dilution ratio, orifice O2 is chosen.

f. Purge Mode

The purge is defined as an approach to clean the SPCS 30 by overflow. It is a simple and effective method to keep the whole system out of particle contamination, especially for orifice flow meters 40 and 42. This mode is recommended to run periodically.

Before this mode is running, flows on mass flow controllers, MFC 52, MFC 54, MFC 56, and MFC 58, are set to some values. To have reverse flow on orifice flow meters 40 and 42, equations 5 and 6 should be satisfied. To avoid pressure transducers (P1, P2, ΔP1, and ΔP2) being damaged by reverse flow, the left sides of equations 5 and 6 should be larger than the right hand sides slightly.

$$Q_{air1}+Q_{makeup1}>Q_{bypassII}+Q_{s2} \quad (5)$$

$$Q_{air2}+Q_{makeup2}>Q_{bypassIII} \quad (6)$$

where $Q_{air1}$ is the dilution air flow on MFC 52, $Q_{makeup1}$ is the makeup air on MFC 54, $Q_{bypassII}$ is the bypass flow on by-pass 88, $Q_{s2}$ is the aerosol flow into orifice flow meter 42, $Q_{air2}$ is the flow on MFC 56, $Q_{makup2}$ is the make up air on MFC 58, and $Q_{bypassIII}$ is the bypass flow on by-pass 150.

When this mode is running, ball valve V4 keeps its original status. Thus, it is closed and no flow is moving through the CPC 48. Therefore, the pressure pulse caused by the start of the vacuum pump 72 does not influence the CPC 48. As a result, it is not necessary for solenoid valve SV to have a delay action. To purge orifice flow meter 40 completely, both ball valves V1 and V2 are picked up in this mode. Table 6 shows the status for valves and vacuum pumps.

TABLE 6

Status of valves and vacuum pump for the purge mode

| | V1 | V2 | V3 | V4 | V5 | V6 | V7 | SV | Vacuum pump I | Vacuum pump |
|---|---|---|---|---|---|---|---|---|---|---|
| Purge | X | X | | | | | | X | X | X |

X - For valves, it means the valve is energized or off the original status. For pumps, it means the pump is on.

Except flow routes upstream of ball valve V4, there is the other flow route in the SPCS 30: HEPA 182→FM 184→ball valve V5→CPC 48. This flow loop keeps the CPC 48 running normally.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An apparatus for use in a system for measuring particles from engine or vehicle exhausts, the apparatus comprising:
    a flow splitter having an inlet, a sample outlet, and a bypass outlet arranged such that a main flow enters the inlet and changes direction to exit the bypass outlet, wherein a sample flow from the main flow exits the sample outlet, the flow splitter further including a guiding element arranged such that particles at a sampling location upstream of the main flow direction change are guided to the sample outlet;
    wherein the guiding element further comprises:
    a tube extending into the flow splitter from the sample outlet, the tube extending to a location upstream of the bypass outlet.

2. The apparatus of claim 1 wherein the guiding element is made of stainless steel.

3. An apparatus for use in a system for measuring particles from engine or vehicle exhausts, the apparatus comprising:
    a flow splitter having an inlet, a sample outlet, and a bypass outlet arranged such that a main flow enters the inlet and changes direction to exit the bypass outlet, wherein a sample flow from the main flow exits the sample outlet, the flow splitter further including a guiding element arranged such that particles at a sampling location upstream of the main flow direction change are guided to the sample outlet;
    wherein the flow splitter further comprises:
    a union tee; and
    wherein the inlet includes a first tube extending into the union tee, the sample outlet includes a second tube extending into the union tee, and the bypass outlet includes a third tube extending into the union tee.

4. The apparatus of claim 3 wherein the second tube extends into the union tee to a location upstream of the bypass outlet to form the guiding element.

5. The apparatus of claim 3 wherein the guiding element further comprises:
    a plate installed in the flow splitter at a location upstream of the bypass outlet, the plate guiding particles from the sampling location to the sample outlet.

6. The apparatus of claim 3 wherein the flow splitter further comprises:
    a bore through reducer connected to the union tee at the sample outlet, the second tube extending through the bore through reducer and into the union tee to a location upstream of the bypass outlet to form the guiding element.

7. The apparatus of claim 3 wherein the guiding element is made of stainless steel.

8. A system for measuring particles from engine or vehicle exhausts, the system including a main flow and a sample flow from the main flow, the sample flow being directed to a particle counter, the system further comprising:
    a flow splitter having an inlet, a sample outlet, and a bypass outlet arranged such that the main flow enters the inlet and changes direction to exit the bypass outlet, wherein the sample flow from the main flow exits the sample outlet, the flow splitter further including a guiding element arranged such that particles at a sampling location upstream of the main flow direction change are guided to the sample outlet;
    wherein the guiding element further comprises:
    a tube extending into the flow splitter from the sample outlet, the tube extending to a location upstream of the bypass outlet.

9. The system of claim 8 wherein the guiding element is made of stainless steel.

10. A system for measuring particles from engine or vehicle exhausts, the system including a main flow and a sample flow from the main flow, the sample flow being directed to a particle counter, the system further comprising:
    a flow splitter having an inlet, a sample outlet, and a bypass outlet arranged such that the main flow enters the inlet and changes direction to exit the bypass outlet, wherein the sample flow from the main flow exits the sample outlet, the flow splitter further including a guiding element arranged such that particles at a sampling location upstream of the main flow direction change are guided to the sample outlet;

wherein the flow splitter further comprises:

a union tee; and wherein the inlet includes a first tube extending into the union tee, the sample outlet includes a second tube extending into the union tee, and the bypass outlet includes a third tube extending into the union tee.

11. The system of claim 10 wherein the second tube extends into the union tee to a location upstream of the bypass outlet to form the guiding element.

12. The system of claim 10 wherein the guiding element further comprises:

a plate installed in the flow splitter at a location upstream of the bypass outlet, the plate guiding particles from the sampling location to the sample outlet.

13. The system of claim 10 wherein the flow splitter further comprises:

a bore through reducer connected to the union tee at the sample outlet, the second tube extending through the bore through reducer and into the union tee to a location upstream of the bypass outlet to form the guiding element.

14. The system of claim 10 wherein the guiding element is made of stainless steel.

* * * * *